US012601688B2

(12) United States Patent
Campbell et al.

(10) Patent No.: US 12,601,688 B2
(45) Date of Patent: Apr. 14, 2026

(54) SILVER COORDINATION POLYMERS FOR MEASURING ARSENIC LEVELS IN WATER

(71) Applicants: THE TRUSTEES OF COLUMBIA UNIVERSITY IN THE CITY OF NEW YORK, New York, NY (US); BARNARD COLLEGE, New York, NY (US)

(72) Inventors: Michael G. Campbell, New York, NY (US); Benjamin C. Bostick, New York, NY (US); Natasha Reich, New York, NY (US)

(73) Assignees: The Trustees of Columbia University in the City of New York, New York, NY (US); Barnard College, New York, NY (US)

( * ) Notice: Subject to any disclaimer, the term of this patent is extended or adjusted under 35 U.S.C. 154(b) by 675 days.

(21) Appl. No.: 18/008,496

(22) PCT Filed: Jun. 7, 2021

(86) PCT No.: PCT/US2021/036086
§ 371 (c)(1),
(2) Date: Dec. 6, 2022

(87) PCT Pub. No.: WO2021/248107
PCT Pub. Date: Dec. 9, 2021

(65) Prior Publication Data

US 2023/0213453 A1 Jul. 6, 2023

Related U.S. Application Data

(60) Provisional application No. 63/196,277, filed on Jun. 3, 2021, provisional application No. 63/035,714, filed on Jun. 6, 2020.

(51) Int. Cl.
*G01N 21/78* (2006.01)
*G01N 33/18* (2006.01)

(52) U.S. Cl.
CPC .......... *G01N 21/78* (2013.01); *G01N 33/182* (2013.01)

(58) Field of Classification Search
CPC .. G01N 21/78; G01N 33/182; G01N 33/1813; G01N 31/22; C02F 2103/06; C02F 1/288; C02F 2101/103
See application file for complete search history.

(56) References Cited

U.S. PATENT DOCUMENTS 7,153,698 B2 12/2006 Voice et al.
7,298,817 B2 11/2007 Chen et al.
(Continued)

FOREIGN PATENT DOCUMENTS

CN 1314998 A 9/2001
CN 101266214 3/2007
(Continued)

OTHER PUBLICATIONS

James K. Kearns et al.,"Expanding Quantification on of Arsenic in Water to 0 μg L with a Field Test Kit: Substituting 0.4% M/V Silver Nitrate as the Colorimetric Reagent; Employing Digital Image Analysis" p. 75, and 1-7, dated Feb. 17, 2018.
(Continued)

*Primary Examiner* — Dennis White
(74) *Attorney, Agent, or Firm* — McNees Wallace & Nurick

(57) ABSTRACT

Measurement devices can be used for identifying concentration of arsenic species in water samples. The measurement devices can take the form of test strips including a substrate with at least one testing region that includes an amount of a testing medium. The silver reagent includes a
(Continued)

polymer framework and a silver component that is stabilized by the framework, yet remains reactive enough to function as a colorimetric sensor for arsenic, e.g., $((Ag(H_2btc))(Ag_2(Hbtc)))_n$. The initially substantially colorless testing medium exhibits a color change response when exposed to arsenic species, e.g., arsine, generated from samples including as little as 5 ppb arsenic, with an increasingly dark color as the concentration of arsenic is increased. Test strips fabricated with the silver coordination polymer display robust stability towards both light and water, allowing for an alternative to mercury-based field test kits in real-world field tests under direct sunlight and high humidity conditions.

18 Claims, 13 Drawing Sheets

(56) References Cited

U.S. PATENT DOCUMENTS

| | | | |
|---|---|---|---|
| 7,336,362 | B2 | 2/2008 | Van Geen |
| 7,446,874 | B2 | 11/2008 | Van Geen |
| 2017/0299502 | A1 | 10/2017 | Schanzer et al. |

FOREIGN PATENT DOCUMENTS

| | | | |
|---|---|---|---|
| CN | 101349673 | | 9/2008 |
| CN | 105911031 | | 4/2016 |
| CN | 105813711 | A | 7/2016 |
| CN | 107792873 | | 8/2016 |
| CN | 106645061 | | 11/2016 |
| CN | 107253799 | | 5/2017 |
| CN | 108195832 | A | 6/2018 |
| GB | 1140149 | | 4/1967 |
| KR | 20180125711 | A | 11/2018 |
| WO | 9013025 | A1 | 11/1990 |

OTHER PUBLICATIONS

Kearns, James Kalman, "Field Portable Methods for the Determination of Arsenic in Environmental Samples" (2010). Open Access Dissertations. 285.

Das J, Sarkar P, Panda J, Pal P. Low-cost field test kits for arsenic detection in water. J Environ Sci Health A Tox Hazard Subst Environ Eng. 2014;49(1):108-15.

Yin, X., & Zhu, L. (2019). High-efficiency photocatalytic performance and mechanism of silver-based metal-organic framework. Journal of Materials Research, 34(6), 991-998.

Boguski, "Understanding Units of Measurement." Environmental Science and Technology Briefs for Citizens. Issue 2 (Oct. 2006) [Retrived on Aug. 9, 2021] Retrived from Internet: <URL:https://cfpub.epa.gov/ncer_abstracts/index.cfm/fuseaction/display.fites/fileid/14285#:~:text=Concentrations%20in%20water%20can%20also,parts%20per%20billion%20(ppb).&text=For%20water%2C%201%20ppm%20%3D%20approximately,equal%20to%206%2C000%20ug%2FI.>.

Fang, X., Zong, B. & Mao, S. Metal-Organic Framework-Based Sensors for Environmental Contaminant Sensing. Nano-Micro Lett. 10, 64 (2018).

"Silver-based arsenic detector" (Columbia) Jan. 7, 2020 (Jan. 7, 2020) [Retrived on Aug. 9, 2021] Retrived from Internet: <URL:https://columbia.resoluteinnovation.com/technologies/CU20205_silver-based-arsenic-detector>.

International Search Report and The Written Opinion, International Application No. PCT/US2021/036086, dated Aug. 9, 2021, mailed Nov. 9, 2021.

Yang JL, Li YJ, Yuan YH, Liang RP, Qiu JD. Target induced aggregation of Ce(III)-based coordination polymer nanoparticles for fluorimetric detection of As(III). Talanta. Dec. 1, 2018;190:255-262.

Wakui Y, Suzuki TM. Visual detection of arsenic using hydride generation followed by reaction with silver bis(2-ethylhexyl)dithiocarbamate retained in a support filter. Anal Sci. 2014;30(6):683-6.

Hashemniaye-Torshizi R, Ashraf N, Arbab-Zavar MH. Hydride generation coupled to microfunnel-assisted headspace liquid-phase microextraction for the determination of arsenic with UV-Vis spectrophotometry. Environ Monit Assess. Dec. 2014;186(12):8381-9.

Hagiwara K, Inui T, Koike Y, Aizawa M, Nakamura T. Speciation of inorganic arsenic in drinking water by wavelength-dispersive X-ray fluorescence spectrometry after in situ preconcentration with miniature solid-phase extraction disks. Talanta. Mar. 2015;134:739-744.

Chauhan S, Upadhyay LSB. An efficient protocol to use iron oxide nanoparticles in microfluidic paper device for arsenic detection. MethodsX. Oct. 27, 2018;5:1528-1533.

Song L, Mao K, Zhou X, Hu J. A novel biosensor based on Au@Ag core-shell nanoparticles for SERS detection of arsenic (III). Talanta. 2016;146:285-90.

Boxi SS, Paria S. Fluorometric sensing of ultralow As(III) concentrations using Ag doped hollow CdS/ZnS bi-layer nanoparticles. Dalton Trans. Dec. 21, 2015;44(47):20464-74.

Pena-Pereira F, Villar-Blanco L, Lavilla I, Bendicho C. Test for arsenic speciation in waters based on a paper-based analytical device with scanometric detection. Anal Chim Acta. Jun. 29, 2018;1011:1-10.

Naujokas MF, Anderson B, Ahsan H, Aposhian HV, Graziano JH, Thompson C, Suk WA. The Broad Scope of Health Effects from Chronic Arsenic Exposure: update on a Worldwide Public Health Problem. Envir Health Persp. Mar. 2013;121(3).

Belitz K, Fram MS, Johnson TD. Metrics for Assessing the Quality of Groundwater Used for Public Supply, CA, USA: Equivalent-Population and Area. Environmental Science & Technology. Jul. 2015.

Cherukuri J, Anjaneyulu Y. Design and Development of Low Cost, Simple, Rapid and Safe, Modified Field Kits for the Visual Detection and Determination of Arsenic in Drinking Water Samples. Intl J of Envir Res and Pub Health. Aug. 2005; 2(2): pp. 322-327.

400

402     providing a substrate 404     administering an amount of a silver reagent to at least a portion of the substrate to form a testing region positioned thereon

500

502 — obtaining a sample of the medium

504 — administering an amount of the sample to a substrate that includes an amount of a silver reagent 506 — measuring a characteristic change of the silver reagent

SILVER COORDINATION POLYMERS FOR MEASURING ARSENIC LEVELS IN WATER

CROSS REFERENCE TO RELATED APPLICATION(S)

This application is a national stage patent application filing of International Application No. PCT/US2021/036086, filed Jun. 7, 2021, which claims the benefit of U.S. Provisional Application Nos. 63/196,277, filed Jun. 3, 2021, and 63/035,714, filed Jun. 6, 2020, which are incorporated by reference as if disclosed herein in their entirety.

BACKGROUND

Intake of arsenic has become both a national and international problem. Arsenic contamination in groundwater affects the health of approximately 150 million people worldwide. In the US, one-fifth of public groundwater supplies contain detectable levels of arsenic. Currently, the issue is most severe in Bangladesh and Vietnam, as well as inner Mongolia and West Bengal in India, resulting at least in part from unconsolidated sediments in geologically young aquifers where arsenic contamination is characterized by sharply varying concentrations of arsenic over short vertical and horizontal distances. These particular areas are low-lying lands with rivers that drain the Himalayas. Weathering and erosion of sulfide minerals occurs during water transport, and as that material is oxidized, arsenic (As) is adsorbed into iron hydroxides. Microbial reduction of Fe(III) oxides releases As into the dissolved phase. There are myriad health problems associated with arsenic intake into the body: liver, blood and lung cancers, mental developmental problems for children, cardiovascular disease, etc.

Referring now to FIG. 1, field testing for arsenic in water is currently conducted using commercially available color-change test strips that use mercury bromide as the active sensing agent, a technology that was invented in the late 1800s. Some field testing of water samples occurs by treating the samples with tartaric acid followed by zinc metal, which converts arsenate [As(V)] and arsenite [As(III)] to arsine gas, $AsH_3$. Arsine reacts with (colorless) mercury(II) bromide embedded in paper test strips, which causes a color change. Despite the fact that mercury bromide is both water-soluble and highly toxic, this remains essentially the only widely-used field test method. Furthermore, the commercial mercury-based test strips typically fail at measurements near the EPA limit for arsenic in water in the US (10 parts per billion, ppb).

There is currently no readily-available commercial alternative to mercury-based arsenic test kits.

SUMMARY

Aspects of the present disclosure are directed to a method of detecting a concentration of arsenic in a medium including obtaining a sample of the medium, administering an amount of the sample to a substrate that includes an amount of a silver reagent, and measuring a characteristic change of the silver reagent. In some embodiments, the characteristic change is a colorimetric change. In some embodiments, the amount of silver reagent is at least sufficient to generate an observable colorimetric change in the presence of 5 ppb arsenic species. In some embodiments, the silver reagent includes a polymeric framework including elemental silver, at least one silver salt, at least one silver compound, or combinations thereof. In some embodiments, the polymeric framework is water insoluble. In some embodiments, the silver reagent includes $((Ag(H_2btc))(Ag_2(Hbtc)))_n$. In some embodiments, the silver reagent is formed by reacting a trimesic acid with at least a first silver compound. In some embodiments, the at least a first silver compound includes silver nitrate. In some embodiments, the medium includes surface water, groundwater, industrial effluent, or combinations thereof.

Some embodiments of the present disclosure include a measurement device for identifying a concentration of arsenic species in a medium including a substrate and a testing region positioned on at least a portion of the substrate, the testing region including an amount of a silver reagent. In some embodiments, the silver reagent includes a framework including elemental silver, at least one silver salt, at least one silver compound, or combinations thereof. In some embodiments, the amount of silver reagent is at least sufficient to generate an observable colorimetric change in the presence of 5 ppb arsenic species. In some embodiments, the framework is water-insoluble plurality of organic linkers, polymeric framework, or combinations thereof. In some embodiments, the silver reagent includes $((Ag(H_2btc))(Ag_2(Hbtc)))_n$. In some embodiments, the silver reagent is formed by reacting a trimesic acid with a silver nitrate.

Some embodiments of the present disclosure include a method of making a measurement device including providing a substrate and administering an amount of a silver reagent to at least a portion of the substrate to form a testing region positioned thereon. In some embodiments, the silver reagent includes a polymeric framework including elemental silver, at least one silver salt, at least one silver compound, or combinations thereof. In some embodiments, the amount of silver reagent in the testing region is at least sufficient to generate an observable colorimetric change in the presence of 5 ppb arsenic species. In some embodiments, the polymeric framework is water insoluble.

In some embodiments, administering an amount of a silver reagent to at least a portion of the substrate to form a testing region positioned includes reacting a trimesic acid with at least a first silver compound to form the silver reagent. In some embodiments, the at least a first silver compound includes silver nitrate. In some embodiments, the silver reagent includes $((Ag(H_2btc))(Ag_2(Hbtc)))_n$.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DESCRIPTION

Figure 1:
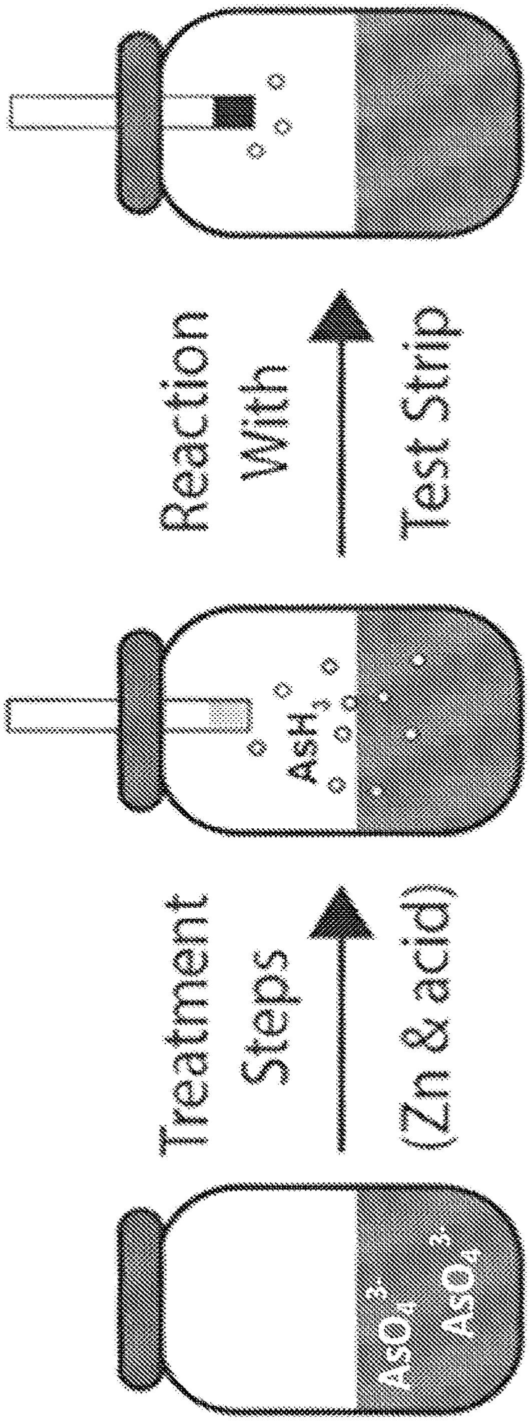
FIG. 1 is a chart of a prior art process of testing water samples for arsenic.
Figure 2:
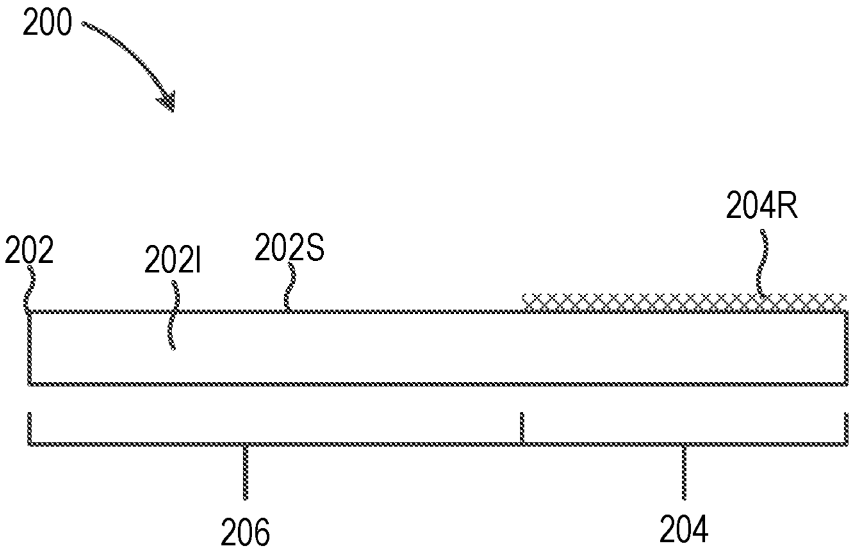
FIG. 2 is a schematic representation of a measuring device for identifying a concentration of a target species in a medium according to some embodiments of the present disclosure.

Referring now to FIG. 2, some embodiments of the present disclosure are directed to a measurement device 200 for identifying a concentration of a target species in a medium. In some embodiments, the target species is an arsenic species. As used herein, the term "arsenic species" refers to elemental arsenic, arsenates, compounds including arsenic, or combinations thereof. In some embodiments, the medium is a liquid. In some embodiments, the liquid is aqueous. In some embodiments, the liquid is water. In some embodiments, the medium is present in nature, e.g., a sample of water from an ocean, lake, river, etc. In some embodiments, the medium includes surface water, groundwater, industrial effluent, or combinations thereof.

In some embodiments, device 200 includes at least one substrate 202. In some embodiments, substrate 202 is composed of cellulose, nitrocellulose, nylon, acrylate polymers, polyvinylidene fluoride, polyethersulfone, polycarbonate, polyester, cellulose acetate, glass fibers, or combinations thereof. In some embodiments, substrate 202 includes at least one testing region 204 that is configured to receive at least a portion of the medium or a sample of the medium, and identify the presence (or concentration) of arsenic species therein, as will be discussed in greater detail below. In some embodiments, testing region 204 is applied on at least a portion of substrate 202, e.g., a surface 202S; incorporated into at least a portion of substrate 202, e.g., interior 202I; or combinations thereof. In some embodiments, testing region 204 includes an amount of a testing medium 204R. In some embodiments, testing medium 204R is configured to produce a characteristic change when contacted with the target species in the medium. In some embodiments, the characteristic change is a colorimetric change. In some embodiments, the colorimetric change is a perceived as a darkening of substrate 202 after administration of a sample of the medium to the substrate. In some embodiments, there is sufficient testing medium 204R to effectively detect as low as 100 ppb, 50 ppb, 10 ppb, or 5 ppb concentrations of target species in the medium. In some embodiments, testing medium 204R is a silver reagent. In some embodiments, the silver reagent includes a framework including elemental silver, at least one silver salt, at least one silver compound, or combinations thereof. The framework serves as a carrier for the silver, which can provide stabilization and further enables tuning of the silver reagent. The silver is stabilized by the framework, yet remains reactive enough to function as a colorimetric sensor, e.g., for arsenic. In some embodiments, the framework is water-insoluble plurality of organic linkers, polymeric framework, or combinations thereof. In some embodiments, there is sufficient silver reagent in testing region 204 to effectively detect, e.g., sufficient to generate an observable colorimetric change, as low as 100 ppb, 50 ppb, 10 ppb, or 5 ppb concentrations of arsenic in the medium. In some embodiments, the extent of the characteristic change increases with the concentration of target species in the medium, i.e., a larger characteristic change is indicative of a higher concentration of target species in the medium.

In some embodiments, the silver reagent includes $((Ag(H_2btc))(Ag_2(Hbtc)))_n$. Without wishing to be bound by theory, $((Ag(H_2btc))(Ag_2(Hbtc)))_n$ includes a single-crystal structure including two independent building units, Ag2 (H2btc)2 and Ag8(Hbtc)12/3, and features a densely-packed 3D network supported by both silver-ligand and silver-silver interactions. In some embodiments, btc is a form of trimesic acid, such as the following structure for $H_3btc$:

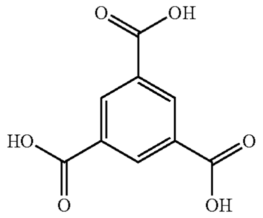 [SMILES: O=C(O)c1cc(C(=O)O)cc(C(=O)O)c1]

In some embodiments, the silver reagent is formed by reacting a trimesic acid with a silver compound and a solvent. In some embodiments, the silver compound is silver nitrate. In some embodiments, the solvent includes an alkyl alcohol, water, or combinations thereof. In some embodiments, the silver reagent is formed by the following reaction pathway:

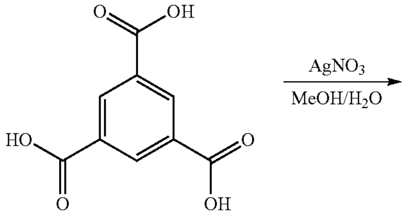

Trimesic Acid ($H_3btc$)

$[\{Ag(H_2btc)\}\{Ag_2(Hbtc)\}]_n$

In some embodiments, device 200 includes a handling region 206 to allow manipulation of device by a user. While FIG. 2 portrays handling region 206 as a portion of substrate 202 itself, the present disclosure is not necessarily limited in this regard, as the handling portion can also be a component separate from the substrate, or a combination thereof.

Figure 3A:
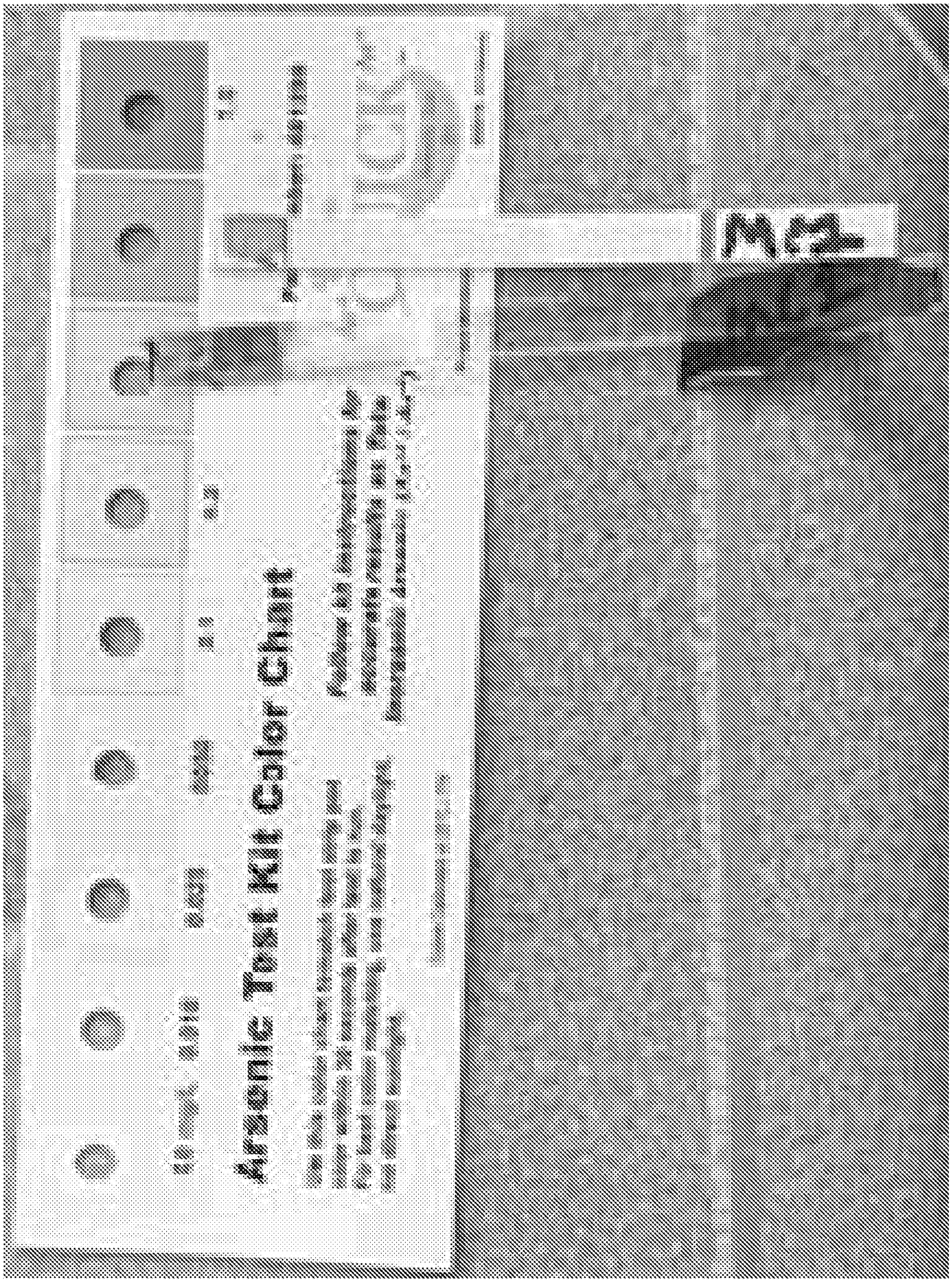
FIG. 3A is an image portraying an exemplary measuring device for identifying a concentration of arsenic species in water according to some embodiments of the present disclosure.
Figure 3B:
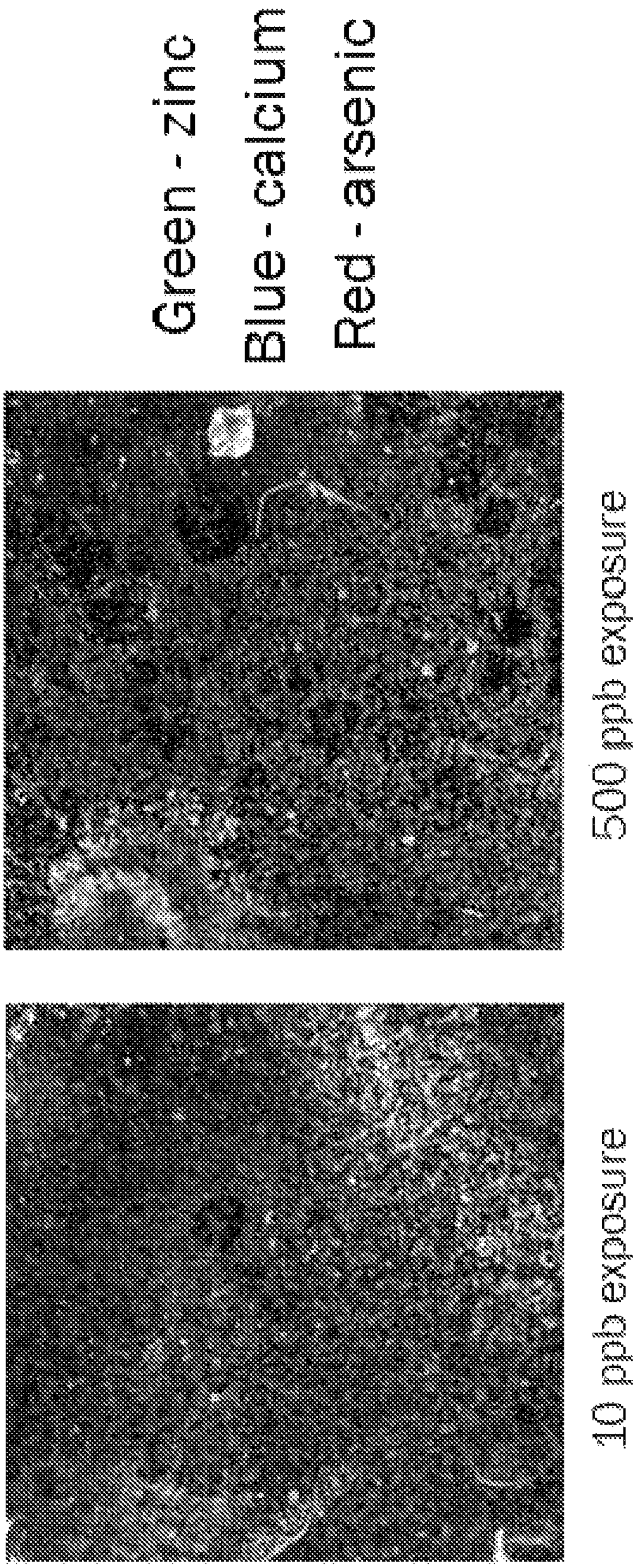
FIG. 3B is an image of microprobe mapping of exemplary measuring devices according to some embodiments of the present disclosure after measuring arsenic species in water.

Referring now to FIGS. 3A-3B, in an exemplary embodiment, test strips were fabricated that are compatible with commercial mercury-based test kits. Replacement of the mercury strips with silver-based strips consistent with embodiments of the present disclosure allowed for use in groundwater field tests in Cambodia. Microprobe mapping of the test strips after testing (@ NSLS-II) is shown in FIG. 3B.

Figure 3C:
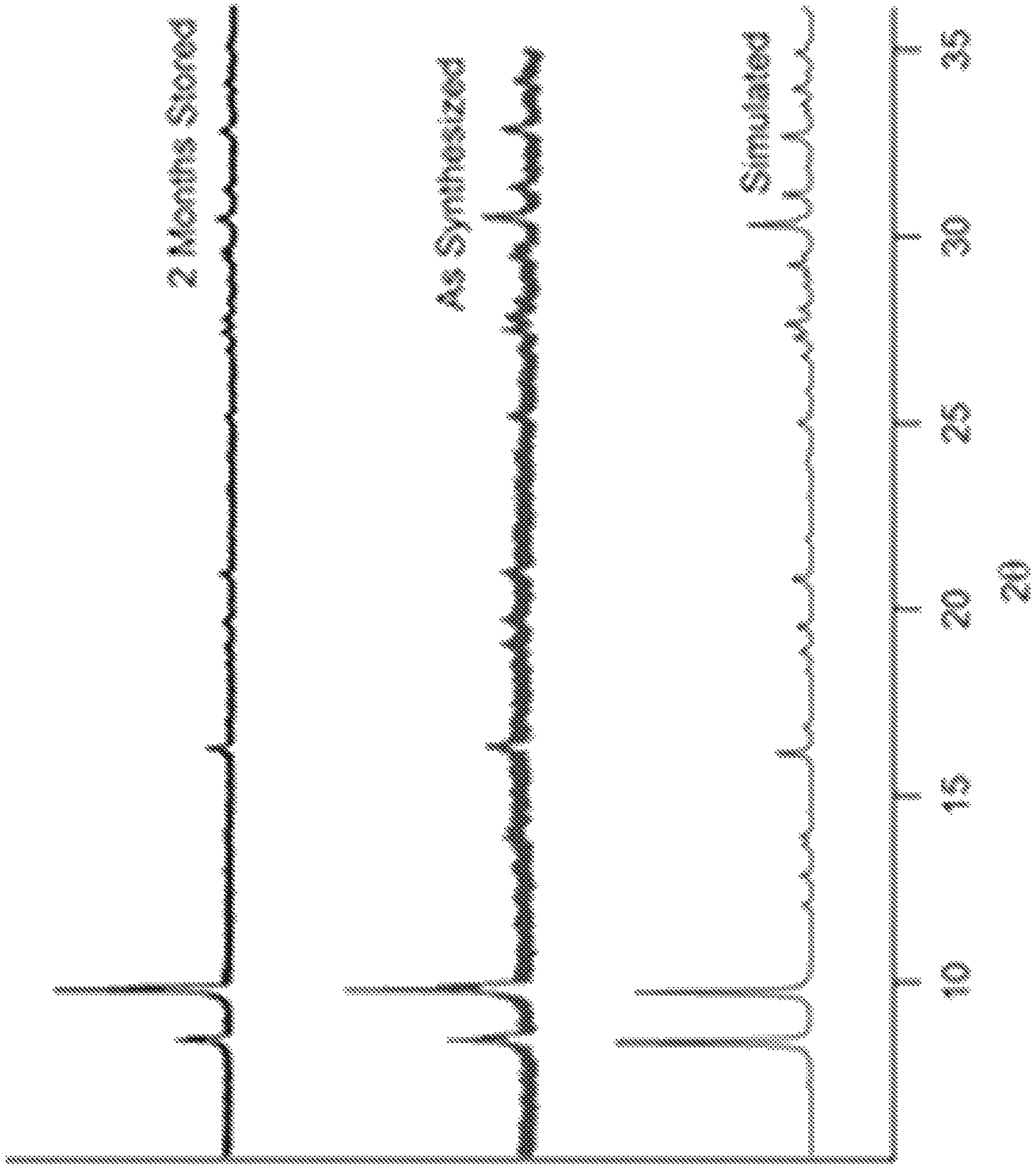
FIG. 3C is a graph exhibiting the stability of silver reagents in the measuring devices according to some embodiments of the present disclosure.
Figure 3D:
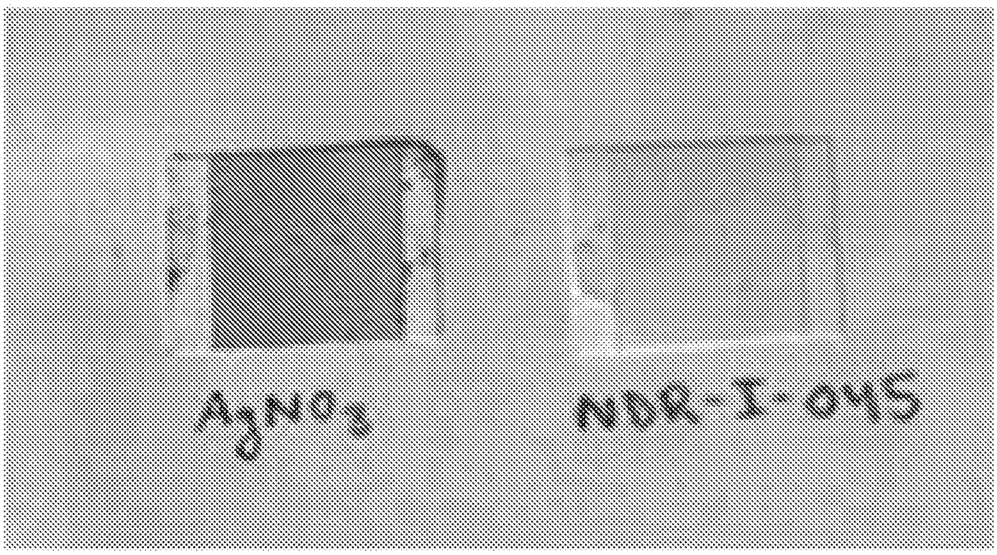
FIG. 3D is an image showing the stability of silver reagents in the measuring devices according to some embodiments of the present disclosure.

Without wishing to be bound by theory, silver coordination polymers and metal-organic frameworks (MOFs) are plentiful, but generally suffer from poor stability, which limits utility in most applications for which MOFs are studied. The crystalline polymer framework of the present disclosure can be used to stabilize silver(I) ions, greatly reducing both photosensitivity and water solubility, while still affording sufficient reactivity to detect arsenic in water samples at low ppb levels. The silver reagents of the present disclosure exhibit no discernable degradation or loss of crystallinity after more than one year of storage under ambient conditions, and are both insoluble in and stable towards water. The silver reagents are also significantly less sensitive towards light than simple silver(I) salts. Referring now to FIGS. 3C-3D, the improved stability (FIG. 3C) and decreased light sensitivity (FIG. 3D, shown after 5 days of ambient light exposure on a windowsill) of the silver reagents of the present disclosure are shown. Test strips fabricated with the silver-based polymer are shown to be effective for field tests of groundwater under real-world operating conditions, and display performance that is competitive with commercially available mercury-based test strips.

Figure 4:
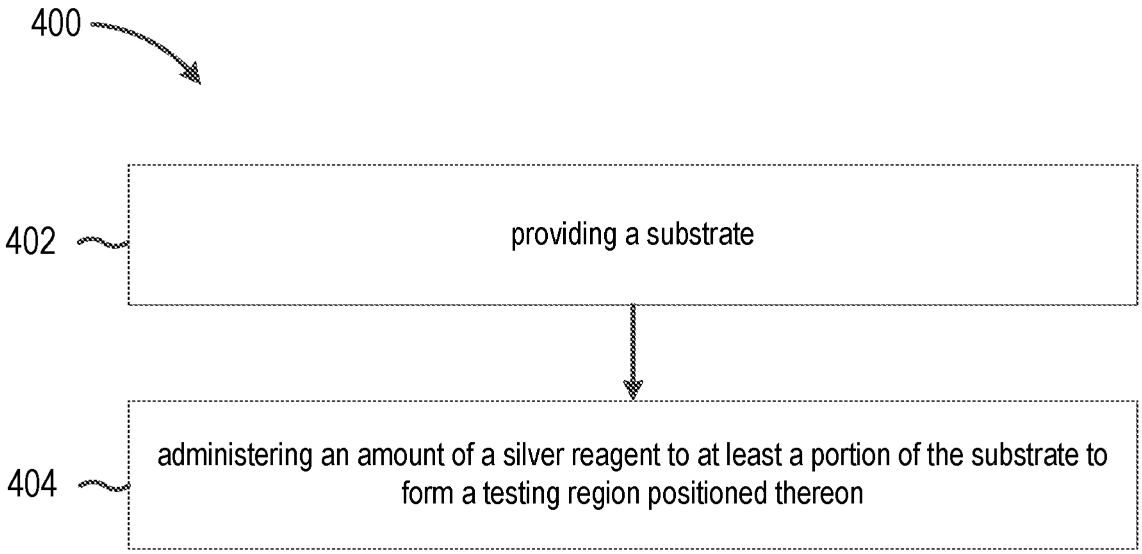
FIG. 4 is a chart of a method of making a measurement device according to some embodiments of the present disclosure.

Referring now to FIG. 4, some embodiments of the present disclosure are directed to a method 400 of making a measurement device. At 402, a substrate is provided. As discussed above, in some embodiments, the substrate is composed of cellulose, nitrocellulose, nylon, acrylate polymers, polyvinylidene fluoride, polyethersulfone, polycarbonate, polyester, cellulose acetate, glass fibers, and or combinations thereof. At 404, an amount of a testing medium is administered to at least a portion of the substrate, forming a testing region positioned on the substrate. As discussed above, in some embodiments, administering 404 testing medium to at least a portion of the substrate includes applying the testing medium on the substrate, e.g., a surface thereof, incorporating the testing medium into a portion of substrate, e.g., an interior thereof, or combinations thereof. In some embodiments, administering 404 testing medium to at least a portion of the substrate includes drop-casting an amount of testing medium to the substrate. As discussed above, in some embodiments, the testing medium includes a silver reagent. In some embodiments, the silver reagent includes a framework including elemental silver, at least one silver salt, at least one silver compound, or combinations thereof. In some embodiments, the framework is water-insoluble plurality of organic linkers, polymeric framework, or combinations thereof. In some embodiments, the silver reagent includes $((Ag(H_2btc))(Ag_2(Hbtc)))_n$. Without wishing to be bound by theory, $((Ag(H_2btc))(Ag_2(Hbtc)))_n$ includes a single-crystal structure including two independent building units, Ag2(H2btc)2 and Ag8(Hbtc)12/3. In some embodiments, btc is a form of trimesic acid, such the following structure for $H_3btc$:

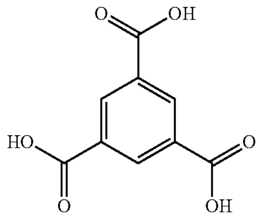 [SMILES: O=C(O)c1cc(C(=O)O)cc(C(=O)O)c1]

In some embodiments, administering 404 testing medium to at least a portion of the substrate includes reacting a trimesic acid with a silver compound and a solvent. In some embodiments, the silver compound is silver nitrate. In some embodiments, the solvent includes an alkyl alcohol, water, or combinations thereof. In some embodiments, the silver reagent is formed by the following reaction pathway:

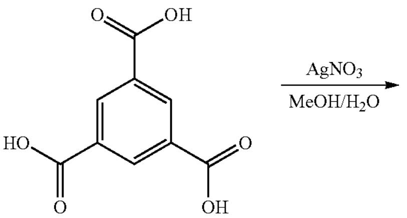

Trimesic Acid ($H_3btc$)

$[\{Ag(H_2btc)\}\{Ag_2(Hbtc)\}]_n$

In some embodiments, the amount of silver reagent in the testing region is at least sufficient to generate an observable colorimetric change in the presence of 5 ppb arsenic species.

Figure 5:
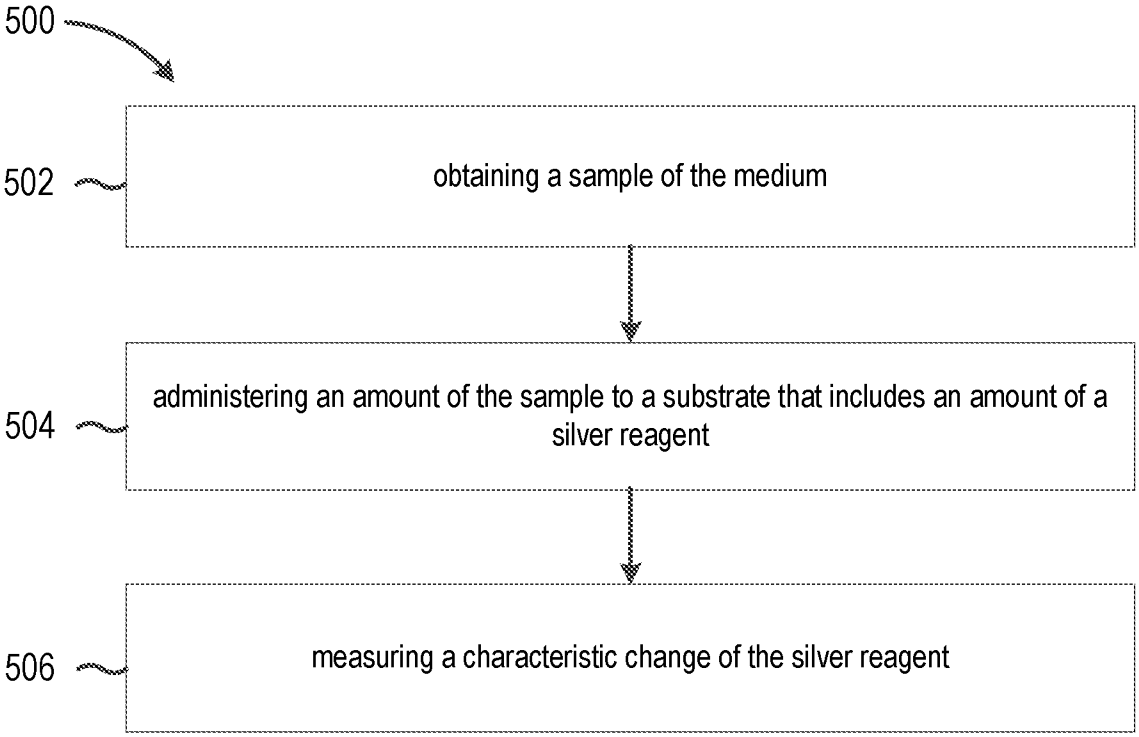
FIG. 5 is a chart of a method of detecting a concentration of arsenic in a medium according to some embodiments of the present disclosure.

Referring now to FIG. 5, some embodiments of the present disclosure are directed to a method 500 of detecting a concentration of arsenic in a medium. As discussed above, in some embodiments, the medium is a liquid. In some embodiments, the liquid is aqueous. In some embodiments, the liquid is water. In some embodiments, the medium is present in nature, e.g., a sample of water from an ocean, lake, river, etc. In some embodiments, the medium includes medium includes surface water, groundwater, industrial effluent, or combinations thereof. At 502, a sample of the medium is obtained by any suitable means. At 504, an amount of the sample is administered to a substrate that includes an amount of a testing medium. As used herein, the term "administered to a substrate" includes direct contact of the sample with the substrate, as well as indirect contact with the substrate wherein one or more components from the overall sample are made to come into direct contact with the substrate. In an exemplary embodiment of administering step 504, a water sample is positioned within a container with the substrate (including the testing medium). Upon application of suitable reagents to the sample, e.g., a Brønsted acid and a chemical reducing agent, component arsenate and arsenite ions in the sample are converted to arsine gas, which escapes from solution into the container and contacts the testing medium on the substrate, resulting in a colorimetric change. In some embodiments, the medium itself is administered in situ, i.e., the medium is brought into contact with the testing medium without first extracting a sample from the medium.

As discussed above, in some embodiments, the testing medium includes a silver reagent. In some embodiments, the silver reagent includes a framework including elemental silver, at least one silver salt, at least one silver compound, or combinations thereof. In some embodiments, the framework is water-insoluble plurality of organic linkers, polymeric framework, or combinations thereof. In some embodiments, the silver reagent includes $((Ag(H_2btc))(Ag_2(Hbtc)))_n$. At 506, a characteristic change of the testing medium, e.g., the silver reagent, is measured. In some embodiments, the characteristic change is a colorimetric change. In some embodiments, there is sufficient silver reactant in or on the substrate to generate an observable colorimetric change in the presence of sufficient to generate an observable colorimetric change, as low as 100 ppb, 50 ppb, 10 ppb, or 5 ppb concentrations of arsenic in the medium.

Figure 6A:
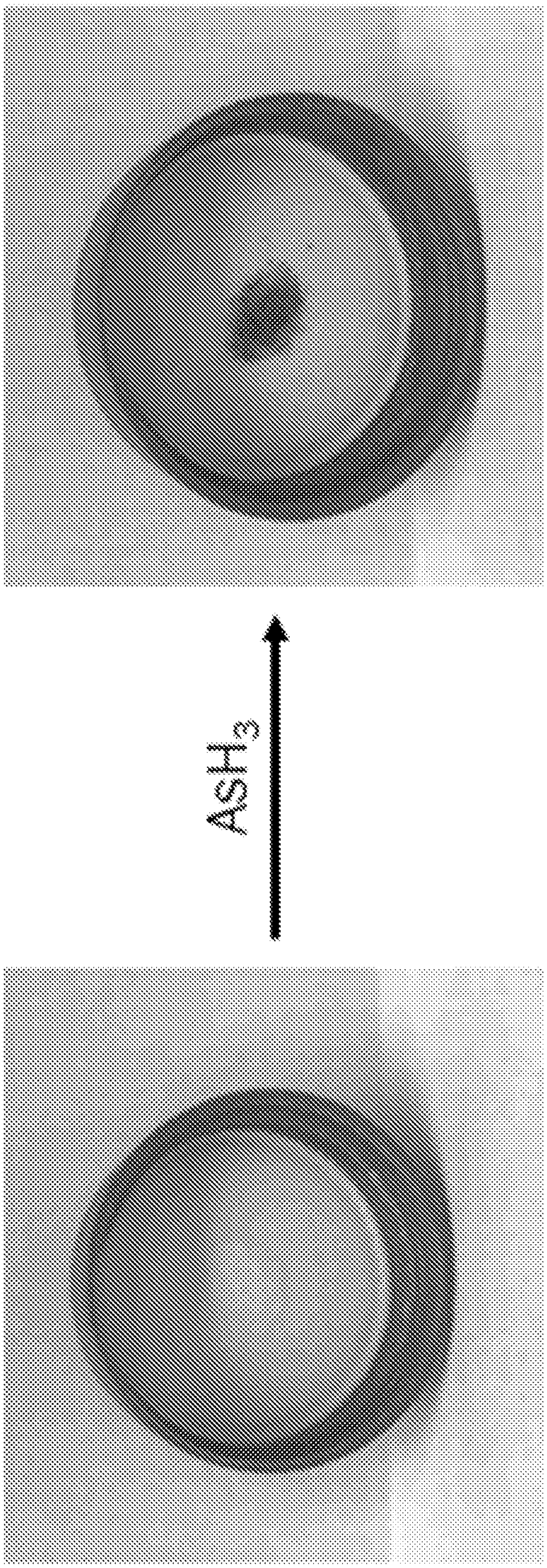
FIG. 6A is an image demonstrating a characteristic change of silver reagents in the measuring devices according to some embodiments of the present disclosure in the presence of arsenic species.
Figure 6B:
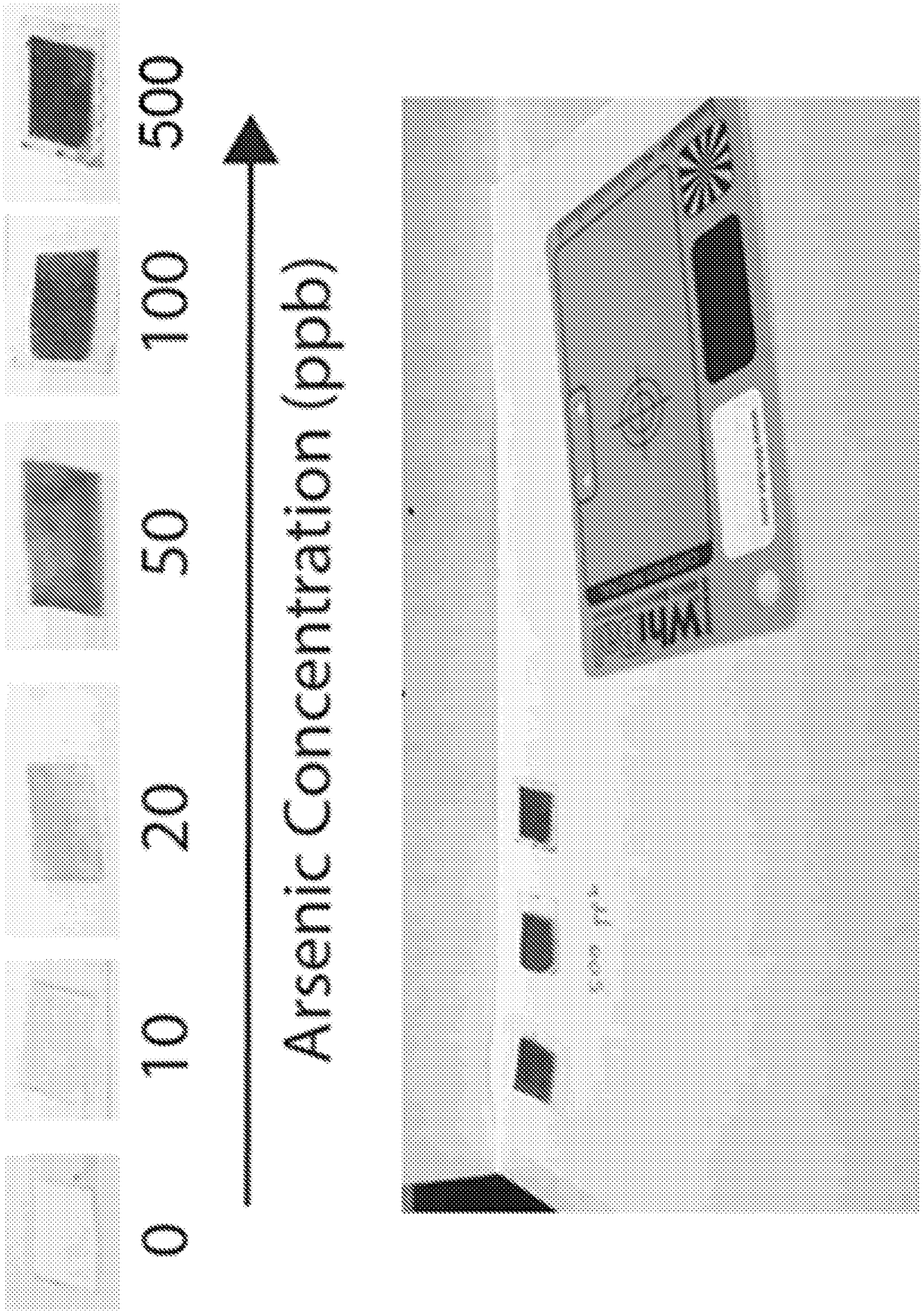
FIG. 6B is an image demonstrating a characteristic change of silver reagents in the measuring devices according to some embodiments of the present disclosure in the presence of arsenic species.
Figure 6C:
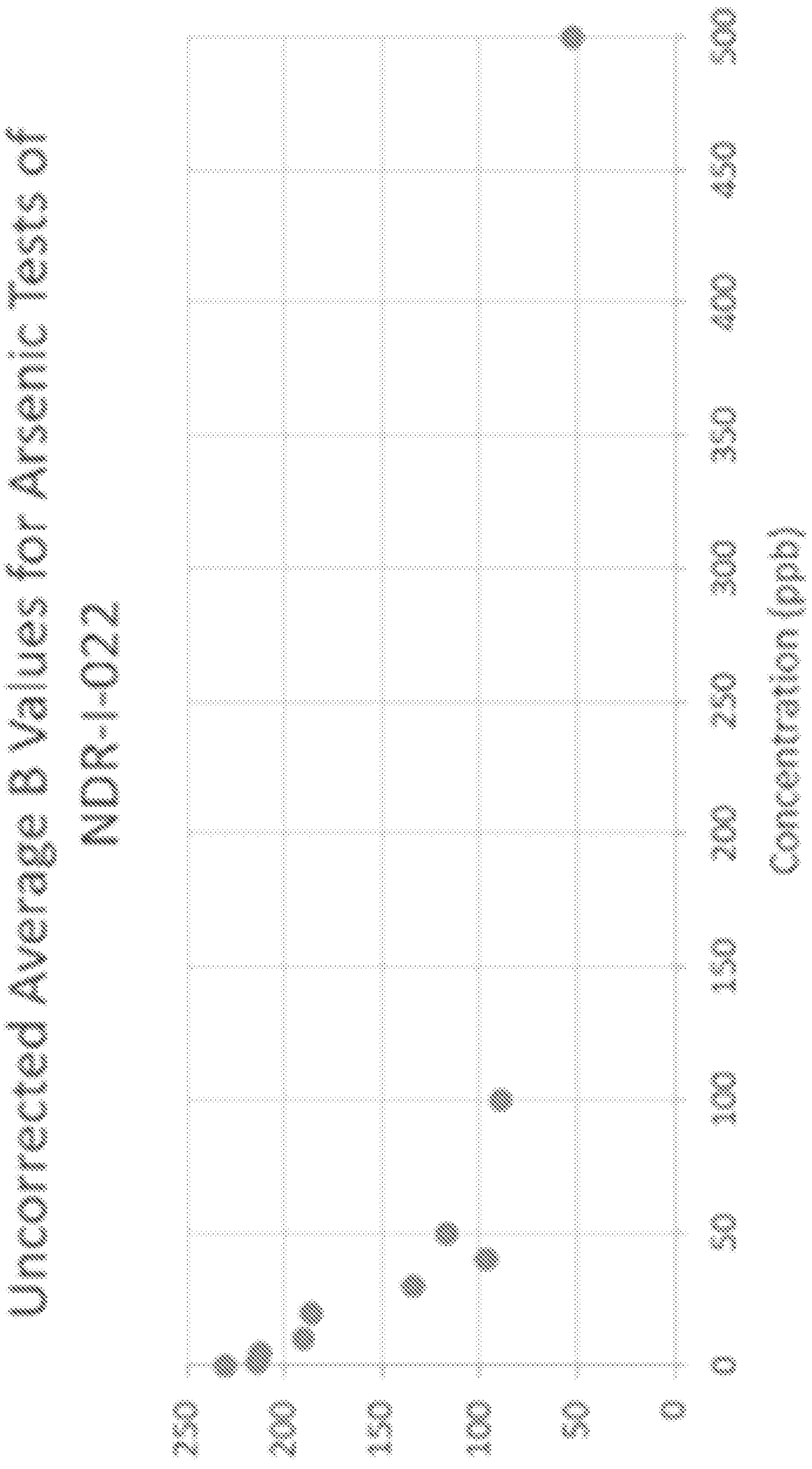
FIG. 6C is a graph showing a characteristic change of silver reagents in the measuring devices according to some embodiments of the present disclosure in the presence of arsenic species.
Figure 6D:
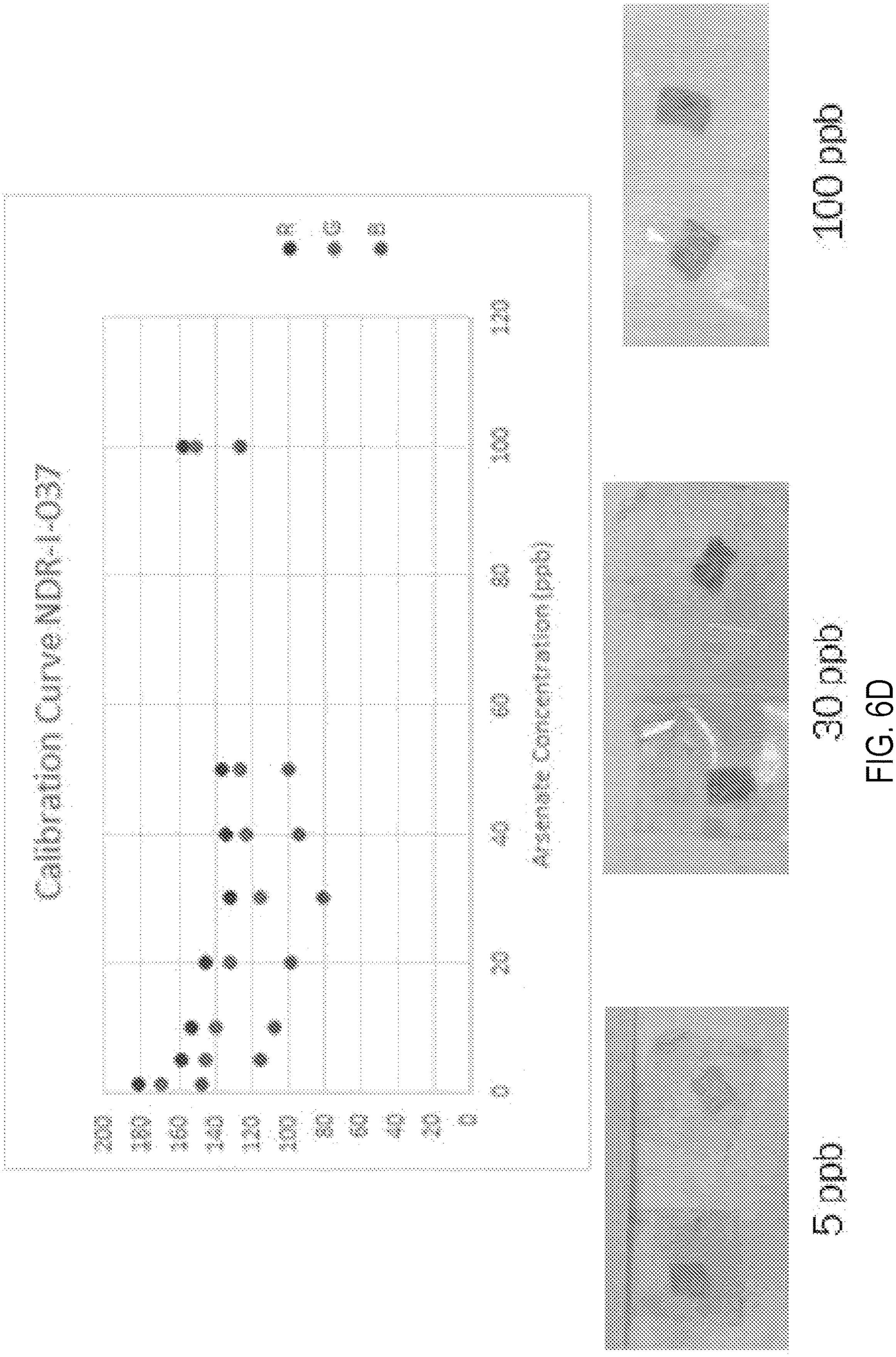
FIG. 6D is a graph and images showing a characteristic change of silver reagents in the measuring devices according to some embodiments of the present disclosure in the presence of arsenic species.

Referring now to FIGS. 6A-6D, as discussed above, silver reagents according to some embodiments of the present disclosure show colorimetric changes in response to the presence of arsenic. Replicate trials (FIG. 6B) were conducted at various arsenic concentrations, and the test squares were photographed under controlled lighting conditions with a color guide for reference. From the digital images, the test squares were pixel averaged, and then the RGB values extracted and plotted against arsenic concentration (FIG. 6C). As can be seen, the initially colorless silver reagent darkens in color upon reaction with arsenic, and the level of color that develops can be used as a readout for the amount of arsenic present in the water sample. Without wishing to be bound by theory, argentophilic interactions commonly found in silver coordination polymers may also help to facilitate reduction in the presence of $AsH_3$. When the amount of silver polymer is decreased, an inversion of response is observed above an arsine concentration threshold, suggestive of a different product formed at higher As:Ag ratios (FIG. 6D).

Analysis of test strips consistent with some embodiments of the present disclosure was performed subsequent to arsenic determination measurements, in order to provide insight into the sensing mechanism. X-ray diffraction (XRD) and X-ray photoelectron spectroscopy (XPS) data indicated that the bulk of the material was unreacted $((Ag(H_2btc))(Ag_2(Hbtc)))_n$, even after tests with arsenic levels as high as 500 ppb. No other diffraction peaks were observed in the powder XRD pattern except those from $((Ag(H_2btc))(Ag_2(Hbtc)))_n$; and, while the XPS data indicated the incorporation of arsenic into the material on the test strip surface, high-resolution scans of the Ag(3d) region showed no discernable differences when comparing $((Ag(H_2btc))(Ag_2(Hbtc)))_n$ before and after reaction with arsine. Taken together, these data suggest that the reaction between $((Ag(H_2btc))(Ag_2(Hbtc)))_n$ and arsine is on the surface of the material, and that a small fraction of the total the silver reagent present on the test strip reacts.

Figure 7:
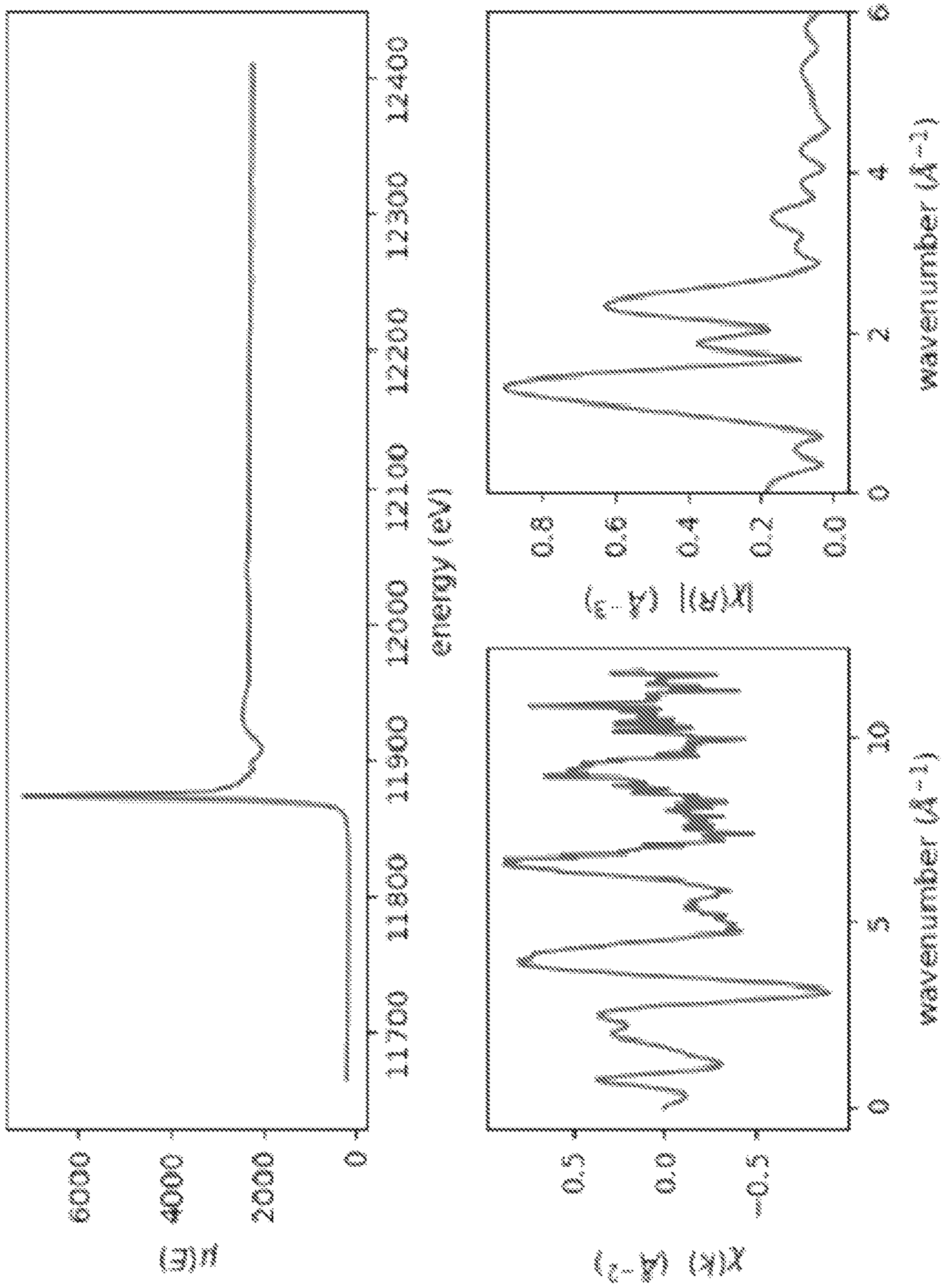
FIG. 7 is a graph showing x-ray absorption spectroscopy (XAS) data for reaction products on test strips according to some embodiments of the present disclosure in the presence of arsenic species.

Referring now to FIG. 7, to gain a more detailed understanding of the reactivity between arsine and $((Ag(H_2btc))(Ag_2(Hbtc)))_n$, the test strips were analyzed via X-ray absorption spectroscopy (XAS) and X-ray fluorescence (XRF) methods, using a synchrotron source. XRF microprobe mapping showed incorporation of arsenic across the area of the test strip, consistent with the XPS data described above. Without wishing to be bound by theory, arsenic K-edge XAS data was perhaps the most informative in revealing the nature of the sensing mechanism: the XANES region of the spectrum showed that arsenic was in the +III oxidation state in the reaction product, indicating a redox reaction in which arsine (with a formal −III oxidation state) is oxidized by the silver(I) ions in $((Ag(H_2btc))(Ag_2(Hbtc)))_n$. The identification of a stable arsenic(III) solid product is exceedingly rare among known arsenic-including materials. The EXAFS region of the arsenic K-edge spectra also indicated a network of arsenic-silver interactions. Without wishing to be bound by theory, the combined data indicated that arsine acts as a reductant towards $((Ag(H_2btc))(Ag_2(Hbtc)))_n$, forming a non-stoichiometric mixed As/Ag solid product on the test strip surface, which is responsible for the observed colorimetric response in arsenic sensing measurements.

Methods and systems of the present disclosure are advantageous to replace mercury-based arsenic test kits of arsenic levels in water with significantly reduced toxicity without sacrificing testing sensitivity. Silver(I) can be used in arsenic testing, replacing mercury(II). Silver(I) salts tend to be both hydroscopic and light-sensitive, with light exposure producing a competing color-change response, and are thus considered unsuitable for use in arsenic testing. However, by including silver in water-insoluble framework, these disadvantages can be overcome. The use of silver reagents of the present disclosure for use in testing strips provides practical advantages as compared to mercury: the silver reagents are less water soluble, are made from significantly less toxic components, and can be tuned for reactivity using rational chemical synthesis. The test strips are responsive to water samples with arsenic levels ranging from single to hundreds of ppb and reliably give a strong colorimetric response at low concentration levels (<50 ppb). The ease of synthesis and fabrication lends itself well to a straightforward manufacturing process.

Water quality monitoring is critical for public health studies and remediation efforts, and the measurement devices of the present disclosure address a significant shortcoming in commercial technologies. Testing agents of the present disclosure will allow for improved testing for water samples with low arsenic levels, which is relevant to meeting EPA standards in the US. Further, there is significant commercial potential for areas such as India where arsenic contamination is a serious public health threat but mercury products are banned due to toxicity.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. A method of detecting a concentration of arsenic in a medium, comprising:
- obtaining a sample of the medium;
- administering an amount of the sample to a substrate that includes an amount of a silver reagent; and
- measuring a characteristic change of the silver reagent,
- wherein the silver reagent includes a polymeric framework including elemental silver, at least one silver salt, at least one silver compound, or combinations thereof.

2. The method according to claim 1, wherein the characteristic change is a colorimetric change.

3. The method according to claim 1, wherein the amount of silver reagent is at least sufficient to generate an observable colorimetric change in the presence of 5 ppb arsenic species.

4. The method according to claim 1, wherein the polymeric framework is water insoluble.

5. The method according to claim 1, wherein the silver reagent includes:

$$((Ag(H_2btc))(Ag_2(Hbtc)))_n.$$

6. The method according to claim 1, wherein the silver reagent is formed by reacting a trimesic acid with at least a first silver compound.

7. The method according to claim 6, wherein the at least a first silver compound includes silver nitrate.

8. The method according to claim 1, wherein the medium includes surface water, groundwater, industrial effluent, or combinations thereof.

9. A measurement device for identifying a concentration of arsenic species in a medium, the device comprising:

a substrate; and a testing region positioned on at least a portion of the substrate, the testing region including an amount of a silver reagent, wherein the silver reagent includes a polymeric framework including elemental silver, at least one silver salt, at least one silver compound, or combinations thereof.

10. The device according to claim 9, wherein the amount of silver reagent is at least sufficient to generate an observable colorimetric change in the presence of 5 ppb arsenic species.

11. The device according to claim 9, wherein the silver reagent includes:

$$((Ag(H_2btc))(Ag_2(Hbtc)))_n.$$

12. The device according to claim 9, wherein the silver reagent is formed by reacting a trimesic acid with a silver nitrate.

13. A method of making a measurement device, the method comprising:

providing a substrate; and administering an amount of a silver reagent to at least a portion of the substrate to form a testing region positioned thereon, wherein the silver reagent includes a polymeric framework including elemental silver, at least one silver salt, at least one silver compound, or combinations thereof.

14. The method according to claim 13, wherein the amount of silver reagent in the testing region is at least sufficient to generate an observable colorimetric change in the presence of 5 ppb arsenic species.

15. The method according to claim 13, wherein the polymeric framework is water insoluble.

16. The method according to claim 13, wherein administering an amount of a silver reagent to at least a portion of the substrate to form a testing region positioned includes:

reacting a trimesic acid with at least a first silver compound to form the silver reagent.

17. The method according to claim 16, wherein the at least a first silver compound includes silver nitrate.

18. The method according to claim 17, wherein the silver reagent includes:

$$((Ag(H_2btc))(Ag_2(Hbtc)))_n.$$

* * * * *